the# United States Patent [19]

Yunis

[11] Patent Number: 5,877,209
[45] Date of Patent: Mar. 2, 1999

[54] HAIR FOLLICLE PROTECTIVE FORMULATIONS

[76] Inventor: Adel A. Yunis, 1600 N.W. 10th Ave., Miami, Fla. 33136

[21] Appl. No.: 745,911

[22] Filed: Nov. 7, 1996

[51] Int. Cl.$^6$ .................................................. A61K 31/34
[52] U.S. Cl. ........................ 514/458; 514/474; 514/717; 514/751
[58] Field of Search .................................. 514/474, 458, 514/717, 751

[56] References Cited

U.S. PATENT DOCUMENTS

| 5,006,331 | 4/1991 | Gaskin ........................................ 424/70 |
| 5,140,043 | 8/1992 | Darr et al. .............................. 514/474 |
| 5,954,667 | 2/1996 | Uchida et al. ....................... 424/195.1 |

FOREIGN PATENT DOCUMENTS 1283050   4/1991   Canada .

OTHER PUBLICATIONS

Hussein, Southern Medical Journal, 86(5), pp. 489–496, May 1993.

*Primary Examiner*—Rebecca Cook

[57] ABSTRACT

The invention relates to hair protective formulations which can be administered to a subject in a manner so as to protect hair follicles against oxidative stress. Additionally, the instant invention relates to a test model for assessing oxidative damage to hair follicles and to determine protection from same.

9 Claims, 3 Drawing Sheets
(3 of 3 Drawing(s) Filed in Color)

CUMENE HYDROPEROXIDE

CONTROL

HAIR FOLLICLE PROTECTIVE FORMULATIONS

FIELD OP INVENTION

The present invention relates to hair protective formulations which can be administered to a subject in a manner so as to protect hair follicles against oxidative stress. Additionally, the instant invention relates to a test model for assessing oxidative damage to hair follicles and to determine protection from same.

BACKGROUND OF THE INVENTION

Hair and Hair Follicles

Visual terminal hair extends above the surface of the skin. Hair is a fully cornified structure that results from complete maturation of follicular matrical cells emanating from the hair follicle (HF).

Hair is not a biologically active structure. However, the HF, and, in particular, the matrix cells of the HF bulb, have high metabolic activity. Matrix cells of human scalp HFs and bone marrow cells have the most active replicating time of any normal tissue.

The scalp HF extends from the epidermis to the bulb situated in the subcutaneous fat. Histologically, the HF may be divided into the upper segment and lower segment. The upper segment is composed of an infundibulum part and isthmus part that extends to the site of the muscle erection. The lower segment extends from the point of attachment of the muscle of erection to the base. The lower segment consists of the stem and bulb.

Indeed, each HF can be considered an independent highly specialized organelle composed of many cell types, such as melanocytes, epidermal and mesenchymal cells. Cells in the HF are in all stages of growth and differentiation during the active anagen (growth) cycle. In addition, each cell type renders different function(s) for the development of the terminal hair. The follicular germ cells, which are the bulbar matrix cells, are responsible for the great mitotic proliferation in the HF.

During development, the cells in the matrix proliferate with an upward migration and differentiation into hair matrix, inner sheath and outer sheath cells. The hair matrix group, located in the central axis of the HF, further differentiates into the cells forming the medulla, hair cortex, and hair cuticle. These cells show a continuous upward migration with keratinization of the cortical and cuticle cells which are essential for the manufacturing process of hair in a growing follicle. (Chase HB, Physiol. Rev. 1954; 34: 113–126, Hashimoto K, Br. J. Dermatol 1970; 83: 167–176. DeVillez RL:In: Current Concept, A Scope Publication, by the Upjohn Co., Kalamazoo, Mich., 1986; pp. 4–27; Takashima I, Kawagihi, I: In: Toda K, et al (eds): Biology and Disease of Hair. Baltimore, Univ. Park Press, 1976; pp. 457–471. Jakubovic H R, Ackerman A B In: Moschella S L, Hurley H J, eds: Dermatology. W. B. Saunders Co., 1992, pp. 3–87).

Oxidative stress produced from environmental chemical and physical agents as well as oxidants produced as by-products of cellular metabolism are extremely toxic to cells. Actively proliferating cells are highly susceptible to oxidant damage. Indeed, oxygen radical stress induced by environmental and/or as a result of endogenous metabolism can be overwhelming and lead to DNA damage. (Poot M, Mutation Res 1991; 256: 177–189).

The effect of oxidative stress and antioxidants on HF has not been previously elucidated. In the present invention, it is postulated that the HF, being an actively proliferating organelle, is highly susceptible to damage by environmental and/or endogenous oxidants.

It is an object of the present invention to provide protective formulations for the protection of HFs against oxidative stress.

It is a further object of the present invention to provide formulations which can be administered to a subject and which provide protection of HFs against damage by environmental and/or endogenous oxidants.

SUMMARY OF THE INVENTION

The present invention relates to formulations which can be administered to a subject and which provide protection to the subject's hair follicles against oxidative stress. Oxidative stress may occur as a result of environmental and physical agents as well as oxidants produced as by-products of cellular metabolism. It is contemplated that the present formulations are effective against damage due to environmental and/or endogenous oxidants. In general, the instant formulations provide protection to hair follicles and protect the hair follicles against the toxic effect of oxygen radical stress. Since hair originates from hair follicles, protection of hair follicles against oxygen radical stress provides a means to maintain hair structure and growth.

The instant formulation comprises at least one antioxidant in a suitable vehicle for administration to a subject. The mode of administration can be any suitable route which allows the at least one antioxidant in the formulation to reach the hair follicles and to provide a protective effect to the hair follicle against oxidative stress. In a preferred embodiment, the present formulation is adapted for topical use, i.e., for direct application to the area of skin of the subject which contains hair follicles.

Thus, formulations have been prepared to provide the HFs in vivo with antioxidants for protection against oxidative stress.

DETAILED DESCRIPTION OF THE INVENTION

In general, the present HF protective formulations comprise an effective amount of at least one antioxidant for providing protection of HFs against oxidative stress. The antioxidants can be any antioxidant compatible and non-toxic to living HFs. In the preferred topical formulations, the amount of the at least one free radical blocking agent, for example, at least one antioxidant can comprise up to about 10% by weight of the formulation, preferably between about 0.5% to about 8% by weight of the formulation and most preferably between about 1.0% to about 5% by weight of the formulation. The at least one free radical blocking agent or antioxidant can comprise one or more free radical blocking agents or antioxidants and preferably contains between 1 and 12, more preferably between 1 and 10 free radical blocking agents or antioxidants. The formulations can contain any number of free radical blocking agents or antioxidants, i.e., between about 1 to 12, 1 to 10 or 2 to 8 wherein the number of free radical blocking agents or antioxidants can be 1, 2, 3, 4, 5, 6, 7, 8, 9, 10, 11 or 12 individual free radical blocking agents or antioxidants. Each of the free radical blocking agents or antioxidants are present in amounts of about 0.01 and 10.0 wt. %, more preferably in amounts of about 0.01 and 0.5 wt. % or in amounts between 0.01 and 0.2% of the formulation. The amount of free radical blocking agent or antioxidant or free radical blocking agents antioxidants present varies with the number of free radical blocking agents or antioxidants and the effectiveness of the antioxidants. In general, the total amount of free radical blocking agents or antioxidants in the formulation is usually between 2% and 8% of the formulation. It is noted that while topical formulations may be preferred, the invention contemplates the possible administration of antioxidants by the oral, subcutaneous or intravenous routes. Such formulations would comprise the at least one antioxidant and a suitable carrier or excipient.

The formulation can contain various compatible surfactants, emollients, humectants, nutrients, fragrances, preservative carriers, and substances to provide consistency. Typical surfactants include: polyoxyethylene ethers such as methyl ether and cetyl ether; polyoxyethylenesorbitan such as mono laureate, mono palmitate and mono oleate; Tergitol and Triton. Typical emollients include: ethoxylated nonionics and their phosphate esters; mineral oil; isopropyl myristate; soya oil; cocoa oil; cotton seed oil and almond oil; hydrocarbons such as petrolatum, waxes and paraffin. Typical humectants such as glycerine, propylene glycol, Peg-600 and polyglyceryl esters. Typical HF nutrients include: vitamin A and derivatives; pantothenic acid and derivatives; and inositol. Typical preservatives include: triclosan; zinc pyrithione; benzalkonium chloride and undecylenic acid. Typical carriers include: water, deionized water, cetyl alcohol, liposome suspension and ethyl alcohol.

The free radical blocking agents or antioxidants used in the present formulations can be obtained from biochemical companies such as: Sigma Chemical Company, P.O. Box 14508, St. Louis, Mo., USA 63178–9916.

Other ingredients such as preservatives, diluents, buffers, nutrients, and pharmaceutically acceptable vehicles, to enhance penetration to the HF, have been added.

The formulations can take various forms including lotions, creams, solutions, emulsions, liposomes, shampoos, and conditioner formulations. They may also include known sun screening compounds to provide the HFs protection against sun damage. The formulations are normally applied topically but can also be formulated for subcutaneous administration and oral intake. The instant HF protective formulation can be administered to any animal which has hair and is generally applied at least once a day, preferably once a day. The amount of the formulation used generally depends upon the age and size of the animal to which the formulation is applied and this amount can be readily determined by the artisan practicing in the pertinent area.

The present formulation is preferably formulated as an emulsion or a gel emulsion. This form which is generally cosmetic enjoys the advantage of having better skin absorption. Active ingredients include: a) a blend of antioxidants and free radicals blocking agents such as: mixed tocopherols, ascorbic acid and ascorbic acid derivatives or ascorbic acid formulations such as disclosed in U.S. Pat. No. 5,140,043, the disclosure of which is incorporated herein; butylhydroxy anisole (BHA); butylhydroxy toluene (BHT); EDTA and similar active materials; b) selected vitamins with a specific effect on the hair and/or the skin (scalp) such as: provitamins; vitamin A and derivatives; pantothenic acid (vit. B5) and derivatives thereof (panthenol); c) specific compounds known to work in the hair mechanism such as: inositol; cystein and derivatives thereof (N-acetyl cysteine); glutathione and similar materials; d) selected antimicrobial additives such as: triclosan, zinc pyrithione; benzalkonium chloride, undecylenic acid and similar materials.

The formulation is made in a way to deliver the above ingredients in the most efficient manner to the scalp and for moisture and emolliency along with suppleness and brilliance to the hair using selected basic ingredients such as: a) an oil phase using mineral oil or a synthetic ester or related materials; mineral oil; isopropyl myristate; soya oil and similar materials, b) emulsifiers such as ethoxylated non-ionics (or their phosphate esters) with possibly some alkylolamide, polyoxyethylen(n); alcohol ether; [polyoxyethylen(10)-oleylether; coconut diethanolamide], c) a coupling agent such as polyols, polyglyceryl esters, PEG-600; glycerine; propylene glycol and similar materials, d) water/preservatives and fragrance.

In a specific formulation for a hair lotion, Tocopherols-phytosterols-ascorbyl palmitate is the main component of the antioxidant system. The tocopherols are from natural origin. The product has the advantage of combining the synergistic power of ascorbic acid with the tocopherols. It has in this way a similar or better behavior than other synthetic antioxidants. Ingredients are included in the formulation as "liposomesystem complex" for better efficiency, but not in the exclusive way. The antimicrobial used is laurtriamoniumchloride (and) benzalkoniumchloride. Procedures are known for making the formulation and the artisan can refer to gel/emulsion/liposome technology. Liposome Suspension can be prepared according to Huang C-H: Biochem. 8: 344–351, 1969.

The following is a formulation that includes several antioxidants as active ingredients. A method of preparation and method of application is also provided.

| Ingredients | % (W/W) |
| --- | --- |
| Polysorbate 20 | 0.5 |
| Eumulgin 0-5 | 2.5 |
| Eumulgin 0-10 | 1.5 |
| Mineral Oil | 3.0 |
| Purton GFD (linoleamide DEA) | 1.0 |
| Citric Acid | 0.1 |
| N-Acetylcysteine | 0.2 |
| Gluthathione | 0.2 |
| Beta-Carotene | 1.0 |
| Vegetable Complex | 2.0 |
| Soybean Oil | 1.0 |
| Soya Lecithin | 0.5 |
| Mixed Tocopherols + Vit. C | 0.2 |
| Panthenol | 0.5 |
| Inositol | 0.2 |
| Methylparaben | 0.2 |
| Cetyl Alcohol | 0.1 |
| Deionized Water | 77.68 |
| Propyl Paraben | 0.1 |
| Propyl Glycol | 7.0 |
| Fragrance | 0.5 |
| Butylated Hydroxyanisole (BHA) | 0.01 |
| Butylated Hydroxytoluene (BHT) | 0.01 |

Manufacturing Procedure
I. Weigh the water in a stainless steel container.
II. Add the ingredients to the water in Step I.
III. Mix ingredients from II with stirring until a suspension of the ingredients is formed.

Method of Application

The present formulation may be preferably applied to the pores of the HFs, gently massaged in and left on for 4–8 hours.

The present invention further comprises a method for determining oxidative damage to hair follicles in mammals comprising assembling a control group of rodents and a test group of rodents. The rodents in both groups are chosen so that their hair follicles are in the anagen phase. Suitable rodents include mice, rats or rabbits. In rats, for example, the anagen phase occurs in 1–11 day old rats and again at 35 days. A test material is applied to both groups of rodents and a protective material to the test group of rodents and a comparison between the test group effect to a control group effect of the test material is conducted.

The test material can be a material which produces oxidative stress, for example, the test material is an antioxidant or a free radical blocking agent or the test material can be a material which induces alopecia.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

ANTIOXIDANTS PREVENT HAIR LOSS PRODUCED BY OXIDANTS

Materials. Sprague Dawley (CD)rats were purchased from Harlam Sprague Dawley Inc., Indianapolis, Ind. Rats were housed and treated in accordance with NIH Guidelines. t-Butyl Hydroperoxide (t-BuOOH), Cumene Hydroperoxide, Butylated Hydroxyanisole (BHA) and Dimethyl Sulfoxide (DMSO) were purchased from Sigma, St. Louis, Mo. Hank's Buffered Solution (HBSS) was purchased from the University of Miami Comprehensive Cancer Center, Miami, Fla.

In the first two examples the organic peroxides, t-BuOOH and cumene hydroperoxide, were used to test their effect on hair growth on the young rat model.

Effect on t-BuOOH on hair growth. Ten four-day old CD rats were randomized in two groups of five rats each.

Group #1 received t-BuOOH (0.07%) in 0.1 ml HBSS s.c. in the head area daily for six days.

Group #2 received HBSS similarly.

Figure 1:
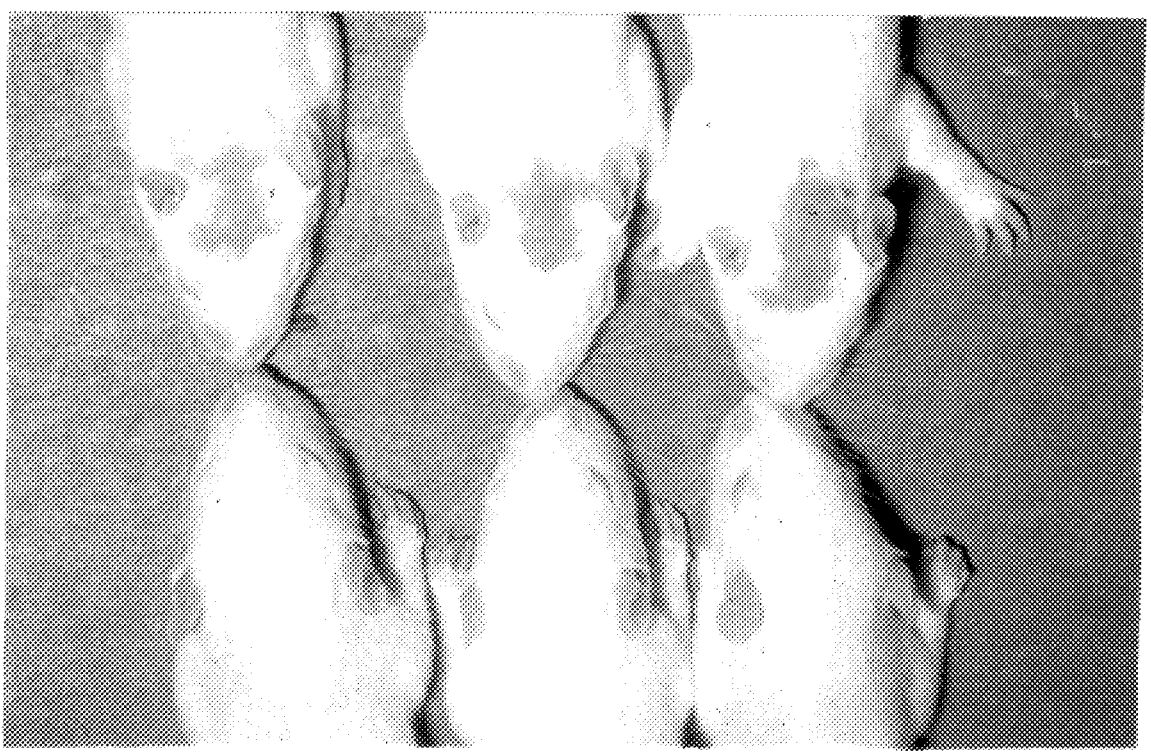
FIGS. 1 and 2 show a comparison of rats treated with oxidant and controls.

Results. On day 10 all the rats in group #1 were alopecic at the site of injection. All the rats in group #2, control, had normal hair growth. FIG. 1.

Effect of cumene hydroPeroxide on hair growth. eight four-day old CD rats were randomized in two groups of four rats each.

Group #1 received cumene hydroperoxide (0.08%) in 0.1 ml HBSS s.c. in the head area daily for six days.

Group #2 received HBSS similarly.

Figure 2:
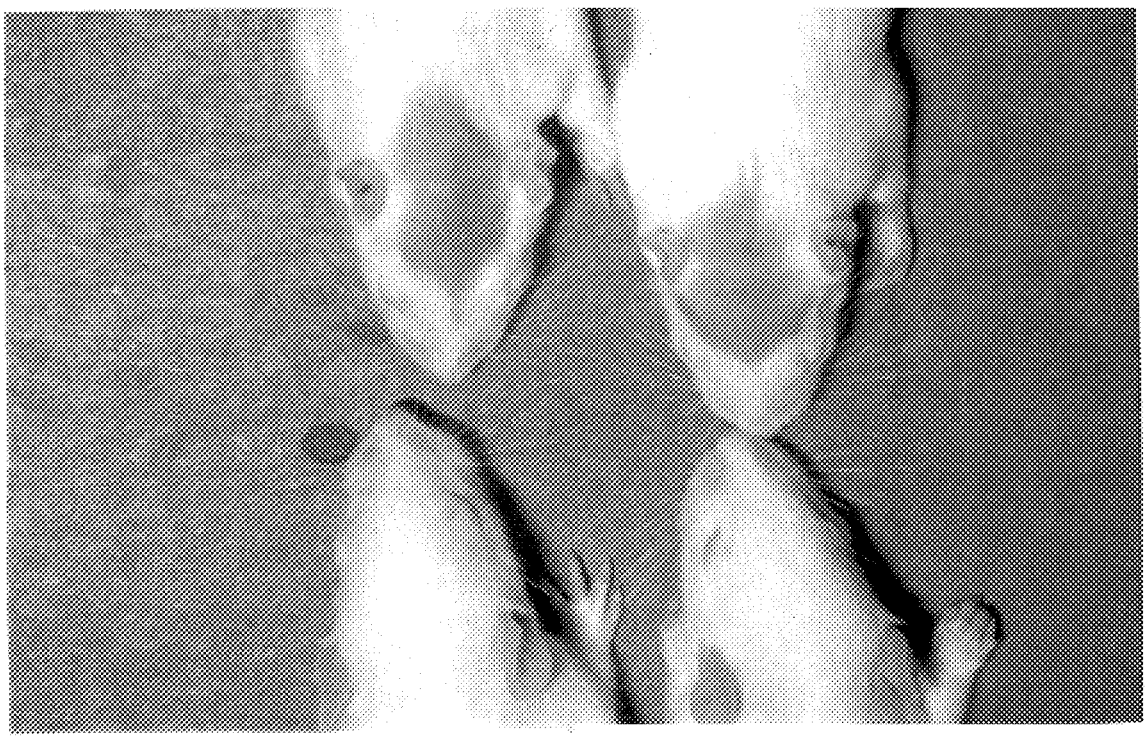

Results. On day 10 all the rats in group #1 were alopecic at the site of injection. All the rats in group #2, control, had normal hair growth. FIG. 2.

Protection by BHA from t-BuOOH-induced hair loss. Eight four-day old CD rats were randomized in two groups of four rats each. All rats received t-BuOOH (0.07%) in 0.1 ml HBSS s.c. in the head area daily for five days. In addition:

Group #1 received 25 $\mu$g BHA s.c. in 0.1 ml of 10% DMSO+90% HBSS in the head area daily for five days 30' prior t-BuOOH.

Group #2 received diluent similarly and served as control.

Figure 3:
FIG. 3 shows a comparison between rats protected with antioxidant and controls.

Results. On day 10 all the rats in group #2 (control) had alopecia at the site of injection. In contrast, all the rats in group #1 had noticeable protection from the t-BuOOH-induced alopecia. FIG. 3.

Although the foregoing invention has been described in some detail by way of illustration and example for purposes of clarity of understanding, it will be obvious to those skilled in the art that certain changes and modifications may be practiced without departing from the spirit and scope thereof as described in the specification and as defined in the appended claims.

What is claimed:

1. A method of protecting hair follicles (HF) against oxidative stress in a subject in need of protection comprising administering to an area in which said follicles are located in an effective amount of a formulation comprising at least one antioxidant or at least one free radical blocking agent wherein the antioxidant or free radical blocking agent is ascorbic-acid, butylated hydroxytoluene (BHT), butylated hydroxyanisole (BHA), a mixture of ascorbic acid and BHT or BHA or a blend of tocopherols and ascorbic acid.

2. The method of claim 1, wherein the formulation is administered topically or orally.

3. The method of claim 2, wherein the formulation is administered in the foam of a lotion, cream, solution, emulsion, liposomes, shampoo or conditioner formulation.

4. The method of claim 1, wherein the formulation is administered as a topical emulsion comprising one or more compatible surfactants or emollients and a suitable carrier.

5. A method according to claim 1, wherein the formulation further comprises one or more humectants, nutrients, preservatives, fragrances, substances to provide consistency, diluents, buffers or vehicles to enhance penetration to the HF.

6. A method according to claim 1, wherein the formulation further comprises a sun screening or sun blocking agent.

7. A method according to claim 4, wherein the formulation comprises a blend of mixed tocopherols and ascorbic acid.

8. A method according to claim 1, wherein the formulation further comprises an antimicrobial additive.

9. The method according to claim 1, wherein the formulation comprises surfactants, mineral oil, citric acid, N-Acetylcysteine, glutathione, Beta-Carotene, vegetable complex, soybean oil, soya lecithin, mixed tocopherols and vitamin C, panthenol, inositol, methylparaben, cetyl alcohol, deionized water, propyl paraben, propyl glycol, fragrance, butylated hydroxyanisole (BHA) and butylated hydroxytoluene (BHT).

* * * * *